(12) United States Patent
Lalonde (10) Patent No.: US 11,259,857 B2
(45) Date of Patent: Mar. 1, 2022

(54) SPRAY NOZZLE DESIGN FOR A CATHETER

(71) Applicant: Medtronic CryoCath LP, Toronto (CA)

(72) Inventor: Jean-Pierre Lalonde, Candiac (CA)

(73) Assignee: Medtronic CryoCath LP

( * ) Notice: Subject to any disclaimer, the term of this patent is extended or adjusted under 35 U.S.C. 154(b) by 678 days.

(21) Appl. No.: 15/922,441

(22) Filed: Mar. 15, 2018

(65) Prior Publication Data

US 2019/0290346 A1    Sep. 26, 2019

Related U.S. Application Data

(62) Division of application No. 15/240,589, which is a division of application No. 13/071,594, filed on Mar. 25, 2011, now Pat. No. 9,439,707.

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00255* (2013.01);
(Continued)

(58) Field of Classification Search
CPC . A61B 18/02; A61B 18/0206; A61B 18/0218; A61B 2018/0212;
(Continued)

(56) References Cited

U.S. PATENT DOCUMENTS 5,281,215 A   1/1994  Milder
6,270,493 B1  8/2001  Lalonde et al.
(Continued)

FOREIGN PATENT DOCUMENTS

CA   2724154 A1   11/2009
CA   2743066 A1    5/2010
CA   2768741 A1    2/2011

OTHER PUBLICATIONS

Reategui, Julio, Tangential Flow Delivery Catheters, MEDRAD Performance. For life., Technical Publication No. 06-004, 2 pages.
(Continued)

*Primary Examiner* — Eun Hwa Kim
(74) *Attorney, Agent, or Firm* — Christopher & Weisberg, P.A.

(57) ABSTRACT

A catheter-based medical device including controlled refrigerant dispersion is disclosed. The device includes a fluid injection tube that carries refrigerant from a coolant supply to the distal portion of the device. A fluid dispersion unit is disposed on the distal end of the fluid tube to control the angle of distribution for refrigerant that is expelled from the fluid injection tube. Controlling the angle of distribution for the refrigerant facilitates dispersion of the fluid in a predetermined spray pattern. The disclosure further relates to cryoablation treatment systems incorporating such a catheter, and to cryoablation treatment methods for tissue treatment to address various conditions suitably treatable with cryoablation.

20 Claims, 8 Drawing Sheets

(52) U.S. Cl.
CPC ............... *A61B 2018/00351* (2013.01); *A61B 2018/00577* (2013.01); *A61B 2018/0212* (2013.01); *A61B 2018/0262* (2013.01)

(58) Field of Classification Search
CPC .... A61B 2018/0281; A61B 2018/0287; A61B 1/00091
See application file for complete search history.

(56) References Cited

U.S. PATENT DOCUMENTS

| | | | |
|---|---|---|---|
| 6,283,959 | B1 | 9/2001 | Lalonde et al. |
| 6,748,872 | B2 | 6/2004 | Parrish |
| 6,895,756 | B2 | 5/2005 | Schmotolocha et al. |
| 7,220,257 | B1 | 5/2007 | Lafontaine |
| 7,354,434 | B2 | 4/2008 | Zvuloni et al. |
| 7,377,620 | B2 | 5/2008 | Wu et al. |
| 7,648,497 | B2 | 1/2010 | Lane et al. |
| 7,780,657 | B2 | 8/2010 | Abboud et al. |
| 2002/0026182 | A1 | 2/2002 | Joye et al. |
| 2002/0045893 | A1 | 4/2002 | Lane et al. |
| 2003/0055416 | A1 | 3/2003 | Damasco et al. |
| 2004/0073203 | A1 | 4/2004 | Yu et al. |
| 2005/0209587 | A1 | 9/2005 | Joye et al. |
| 2006/0270981 | A1* | 11/2006 | Capuano ............ A61B 18/02 604/113 |
| 2007/0059216 | A1 | 3/2007 | Larsson et al. |
| 2008/0171974 | A1* | 7/2008 | Lafontaine ........ A61M 25/1034 604/96.01 |
| 2009/0118723 | A1* | 5/2009 | Lalonde ............ A61B 18/02 606/21 |
| 2009/0209949 | A1* | 8/2009 | Ingle ................ A61B 18/02 606/21 |
| 2009/0234345 | A1* | 9/2009 | Hon ................. A61B 18/02 606/21 |
| 2010/0094270 | A1 | 4/2010 | Sharma |
| 2010/0130970 | A1* | 5/2010 | Williams ........ A61M 25/10185 606/21 |
| 2011/0184398 | A1 | 7/2011 | Desrochers |

OTHER PUBLICATIONS

Extended European Search Report, dated Jul. 22, 2014, 6 pages, Application No. 12763944.1.

* cited by examiner

SPRAY NOZZLE DESIGN FOR A CATHETER

CROSS-REFERENCE TO RELATED APPLICATION

This application is a divisional of and claims priority to patent application Ser. No. 15/240,589, filed Aug. 18, 2016, entitled SPRAY NOZZLE DESIGN FOR A CATHETER, which is a divisional of and claims priority to patent application Ser. No. 13/071,594, filed Mar. 25, 2011, entitled SPRAY NOZZLE DESIGN FOR A CATHETER, issued as U.S. Pat. No. 9,439,707, the entirety of all of which is incorporated herein by reference.

STATEMENT REGARDING FEDERALLY SPONSORED RESEARCH OR DEVELOPMENT n/a

TECHNICAL FIELD

The disclosure relates to catheter-based medical devices, and more particularly to mechanisms and methods for controlling the dispersion of cryogenic fluid from a cryoablation catheter.

BACKGROUND

Many medical procedures are performed using minimally invasive surgical techniques wherein one or more devices are inserted through one or more small incisions into a patient's body. For example, a cardiac arrhythmia may be treated through selective ablation of cardiac tissue to eliminate the source of the arrhythmia. Radio frequency energy, microwave energy, laser energy, extreme heat, or extreme cold may be provided by the ablation device to ablate the tissue.

One category of such ablation devices is the minimally-invasive, catheter-based device that is introduced into the vasculature and used to treat tissue by cooling contact. Such catheter-based devices, henceforth generically referred to herein simply as "catheters" have an elongated body through which a cooling fluid circulates to a tip portion which is adapted to contact and cool tissue. The cooling fluid used with such catheters may be a low temperature fluid, or cryogens. In general, the catheters may be used to lower the temperature of tissue, such as cardiac wall tissue, to an extent such that signal generation or conduction ceases and allows one to map or confirm that the catheter is positioned at a particular lesion or arrhythmia conduction site. More recently, cryoablation catheters have been configured for ablation treatment, to cool the tissue to a much lower level at which freezing destroys the viability of the tissue, and, in the case of cardiac tissue, permanently removes it as a signal generating or signal conducting locus. Such devices are also useful for tissue destruction in other contexts, such as the ablation of tumorous, diseased, precancerous or congenitally abnormal tissue.

The catheters may be adapted for endovascular insertion, or for insertion along relatively confined pathways, for example through a body lumen, or through a small incision to and around intervening organs, to reach an intended ablation site. As such, they are characterized by a relatively elongated body through which the cooling fluid circulates, and a tip or distal end portion where the cooling is to be applied. The requirement that the coolant be localized in its activity poses stringent constraints on a working device. For example, when the catheter contact must chill tissue to below freezing, the coolant itself must attain a substantially lower temperature. The rate of cooling is limited by the ability to supply coolant and circulate it through the active contact region, and the efficacy of the contact region itself is further limited by geometry and physical properties that affect its ability to conduct heat into the tissue.

Furthermore, it is generally desirable to control the direction of the cryogenic fluid flow to only the target tissue sites. In some procedures, a spot tissue ablation procedure—where the fluid flow is directed at a specific site—may be acceptable. For other procedures, it may be more therapeutically effective if the fluid flow is directed along a predetermined line, or a single elongate ring or linear lesion created in a single ablative step. However, the small dimensions of the catheter assembly have the result that flow conditions existing within the catheter tip are turbulent and chaotic. This arises in part because the high pressure release of fluid in a relatively small chamber at the tip of the catheter and/or its recirculation back via a return conduit from the tip region involve relatively turbulent fluid flow conditions, so that the precise control of directional contact on the tissue may be subject to rather wide variations. Thus, while conventional catheter arrangements have been found to provide a high level of cooling, the introduction at high pressure into the small expansion chamber results in cavitation, turbulence and irregular fluid flow evolving in the short distance and brief time between the jet spray of expanding coolant and the lower pressure conditions existing at the proximal end of the chamber adjacent the coolant return passage.

Accordingly, cryoablation catheters could benefit from improved techniques and devices for providing uniform and evenly controlled flow of the thermal transfer fluid onto the targeted tissue cells.

SUMMARY

The disclosure generally describes a cryoablation catheter for use in tissue ablation. The catheter comprises an elongate supply lumen, or injection tube, which carries a cryofluid or refrigerant from a refrigerant supply unit. Typically, a source of refrigerant is connected to the proximal end of the supply lumen and a cryochamber, or expandable chamber, is located at the lumen's distal end. In some embodiments, the source of refrigerant is a fluid that is ejected from the supply lumen through an orifice coupled at a distal portion of the lumen and housed within the expandable chamber. The catheter also comprises a fluid dispersion unit that is also housed, at least partially, within the expandable chamber. At the predetermined pressures to which the cryoablation fluid is subjected, the construction of the fluid dispersion unit must be so designed and dimensioned to disperse a definite amount of fluid within certain limits. The dispersion unit of the present disclosure serves to evenly distribute the refrigerant exiting the distal end of the supply lumen across at least some portion of the interior of the expansion chamber.

Accordingly, embodiments of the disclosure teach fluid dispersion units which control the distribution of fluid flowing therethrough. In one example, the fluid dispersion unit comprises a flow distribution sleeve that induces in a fluid expelled from there sleeve a motion having a predetermined pattern. In another example, the fluid dispersion unit comprises a deflection member that redirects the direction of flow of a fluid in a predetermined pattern. In yet another example, the fluid dispersion unit comprises an arrangement of the flow distribution sleeve and the deflection member.

In accordance with an embodiment of the disclosure, a fluid nozzle is disposed on the distal end of a supply lumen. The fluid nozzle is disposed within a fluid dispersion unit in a predetermined arrangement. In some examples, the arrangement of the fluid nozzle and the fluid dispersion unit causes fluid flowing from the nozzle to undergo a predetermined motion.

Other embodiments disclose a catheter which includes an outer tubular member capable of insertion into the vessels of the body. An expandable chamber, such as a distendable balloon, is disposed at the distal end of the outer tubular member. An inner tubular member substantially spanning the length of the outer tubular member may be employed to carry a fluid to the interior of the expandable chamber. A fluid nozzle is disposed on the distal end of the inner tubular member. A fluid dispersion unit is provided in fluidic-communication with the fluid dispersion unit for controlling the direction of dispersion of the fluid.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

It is to be understood that both the foregoing general description and the following detailed description are exemplary and explanatory only and are not restrictive of the disclosure. The accompanying drawings, which are incorporated in and constitute a part of this specification, illustrate several embodiments of the disclosure and together with the description, serve to explain the principles of the disclosure.

In one aspect, the catheter described herein can be used for performing ablation near or within the pulmonary veins of the heart where an ablation band that may have a circumferential or linear geometry across the targeted tissue is formed. However, the devices described herein are not limited to cardiac applications.

To better understand the environment in which the devices and methods of the present disclosure are used, a general overview of an ablation procedure is believed to be useful. The example pertains to a catheter-based ablation treatment of cardiac arrhythmias, wherein a specific area of cardiac tissue having aberrant conductive pathways, such as atrial rotors, emitting or conducting erratic electrical impulses, is cold-treated through energy transfer derived from thermodynamic changes occurring in the flow of a cryogenic fluid through the catheter device. This energy transfer creates a net transfer of heat from the target tissue to the device, typically achieved by cooling a portion of the device to very low temperature through conductive and convective heat transfer between the cryogen and target tissue.

Figure 1:
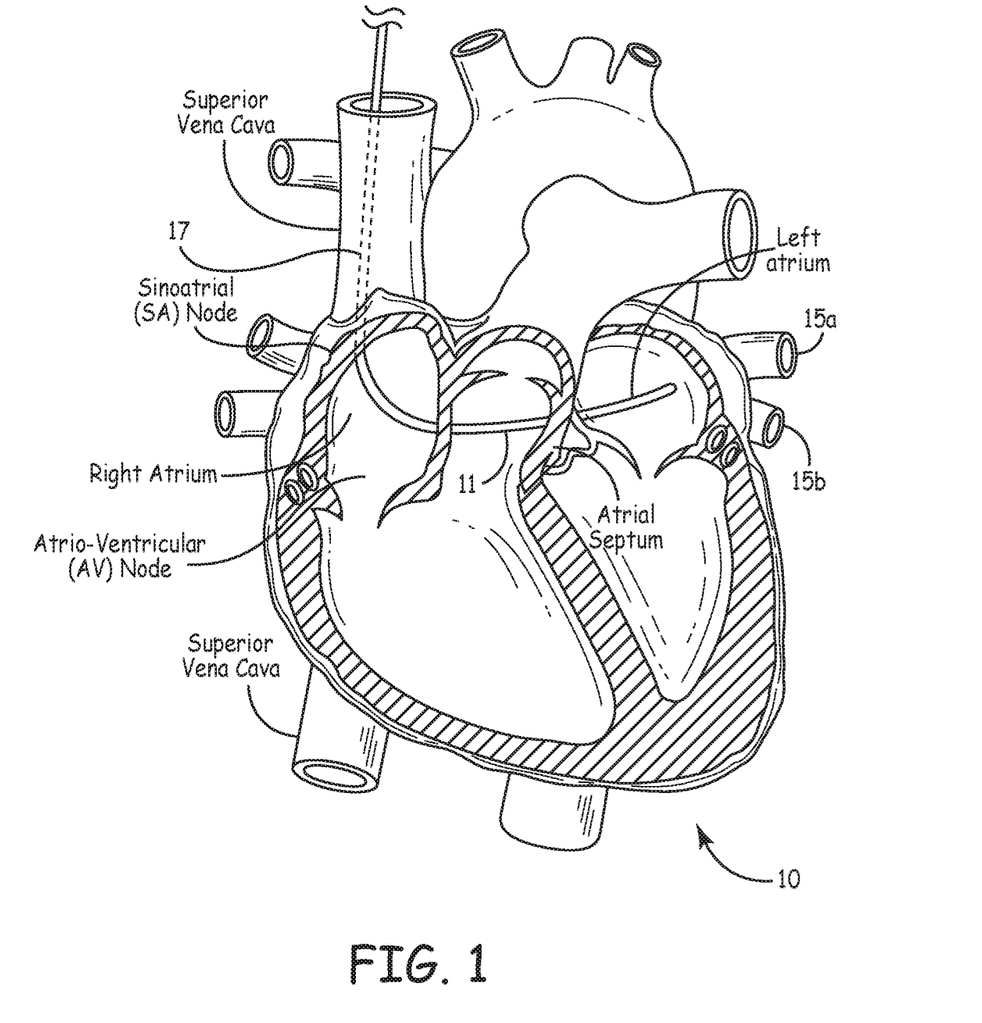
FIG. 1 illustrates an exemplary ablation catheter of the present disclosure as it would be deployed and used for an ablation procedure.

Referring to FIG. 1, the treatment to be accomplished with the devices, systems and methods described in this disclosure is illustrated. FIG. 1 shows a cutaway view of the human heart 10, showing the major structures of the heart 10 including the left and right atria, and the pulmonary veins 15a, 15b. The atrial septum separates the left and right atria. The fossa ovalis 11 is a small depression in the atrial septum that may be used as an access pathway to the left atrium from the right atrium, such as with a transeptal puncture device and transeptal sheath. The fossa ovalis 11 can be punctured, and easily reseals and heals after procedure completion. In a patient suffering from atrial fibrillation, aberrant electrically conducive tissue may be found in the atrial walls, as well as in the pulmonary veins 15a, 15b. Ablation of these areas, referred to as arrhythmogenic foci (also referred to as drivers or rotors), is an effective treatment for atrial fibrillation. Systems, devices and methods of the present disclosure provide means of creating lesions, including lesions to surround the pulmonary vein ostia, and are deployed to identify and ablate the driver and rotor tissue.

To accomplish this, a catheter (FIG. 2) is inserted into the right atrium, preferably through the inferior vena cava or through the superior vena cava. The catheter is sized for advancement through the patient's vasculature. As an example, which is not intended to be limiting, an exemplary catheter may have a shaft having a diameter ranging from 7-9 Fr, with the shaft length ranging from 100-125 cm and the overall length being in the range of 140-160 cm. The catheter may be passed through transeptal sheath, which may or may not be a deflectable sheath since the catheter preferably includes a deflectable distal portion. When passing into the left atrium, the transeptal sheath passes through or penetrates the fossa ovalis 11, such as over guide wire 17 which may have been placed by the transeptal puncture device. The catheter is inserted over guide wire 17 and through transeptal sheath such that its distal end enters the lumen of right superior pulmonary vein 15a, 15b. The catheter carries an ablating element, such as an expandable chamber (FIG. 2) into the left atrium. The expandable chamber is transitioned to expand to a maximal diameter by, for example inflation, such that the expandable chamber is in contact with the walls of the target tissue e.g., pulmonary vein ostia to occlude the vein.

An electrical mapping procedure may be performed to identify or confirm the location of the target cardiac tissue. Next, a treatment medium (e.g., cryogenic fluid) provided by a source external to the patient, is provided through the catheter into the ablating element to ablate the neighboring tissue and form a lesion. The system may utilize various systems, such as the Joule-Thompson effect, to achieve the cooling including the exemplary systems described in commonly-assigned U.S. Pat. No. 7,780,657 to Abboud et al., entitled "COOLING SYSTEM," which issued on Aug. 24, 2010, and is incorporated herein by reference in its entirety. For example, in one embodiment, a pressurized liquid or a liquid/gas mixture passes into a region where it is enabled to evaporate. In other embodiments, a cryogenic fluid delivered to an expandable balloon is a pressurized gas wherein expansion of the pressurized fluid effects the cooling.

Accordingly, the cooling methods may allow for expansion of a compressed fluid independent of whether there is a phase change and/or may include phase changes from liquid to gas or an expanded gas being cooled to such an extent that a portion of the expanded gas actually condenses into a liquid phase. Suitable cryogenic fluids will be non-toxic and include nitrogen, nitrous oxide, carbon dioxide, and the like. By delivering the cryogenic fluid through the catheter body, the balloon can be expanded and cooled in order to effect treatments according to the present disclosure.

The created lesions may be segmented and localized. The lesions may be linear or curvilinear, circumferential and partial circumferential, and/or continuous or discontinuous. The lesions created by the ablation catheters are suitable for inhibiting the propagation of inappropriate electrical impulses in the heart 10 for prevention of reentrant arrhythmias. In general, the catheter ablation therapy will disrupt the electrical pathways in cardiac tissue to stop the emission of and/or prevent the propagation of erratic electric impulses.

Figure 2:
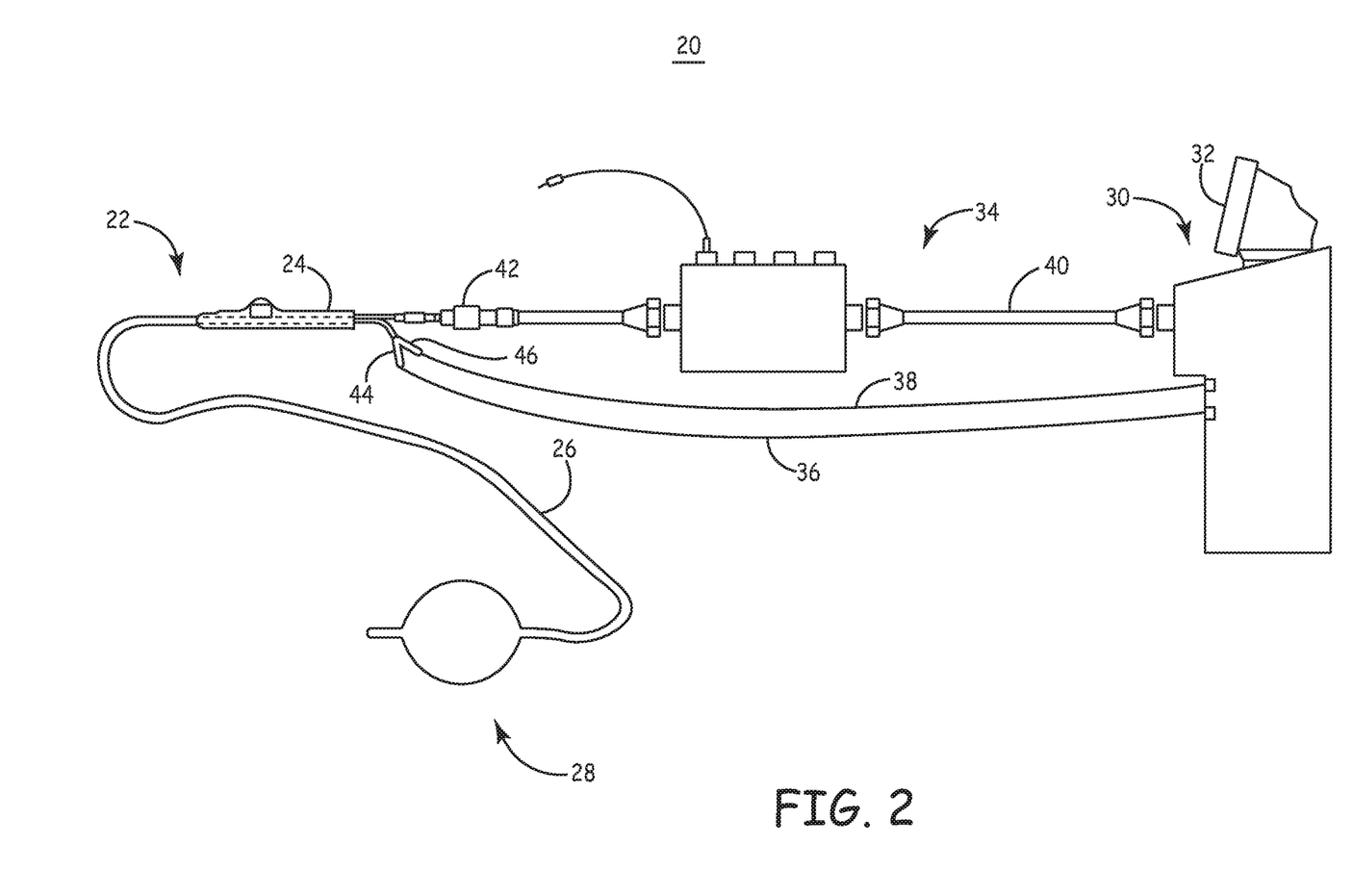
FIG. 2 shows a cryogenic treatment system in accordance with an embodiment of the disclosure.

FIG. 2 shows a cryogenic treatment system 20 in accordance with an embodiment of the disclosure. System 20 includes a treatment catheter 22 having a handle 24, and elongated cryogen transporting body 26 and a catheter tip 28 (described in more detail in FIG. 3). The catheter 22 is connected by various conduits or cables to a console 30 which may, for example, have a display monitor 32 and other data entry or display accessories such as a keyboard, a printer and the like. Operation of the console 30 involves controlling the timing and amount of coolant injected through the catheter 22 at a defined injection pressure, which may be a pressure of about 400 psig, for example. The entire catheter 22 may be dimensioned to fit in a No. 14 French introducer or smaller. The console 32 is connected to the catheter 22 by various lines 34 which may include a coolant injection line 36, a coolant return line 38 and electrical cabling 40 which carries outputs of various cardiac sensing, thermal sensing, mapping or other elements as may be used for catheter treatment or monitoring. As shown, the handle 24 is equipped with input ports for an electrical connector 42, a coolant injection tube connector 44, and a return tube connector 46. These connect by various internal junctions or tubes passing through the handle and elongated body 26 to the distal tip of the catheter. The handle 24 may also include various control assemblies, e.g., switches or valves, as well as safety detection or shutdown elements (not illustrated).

Figure 3:
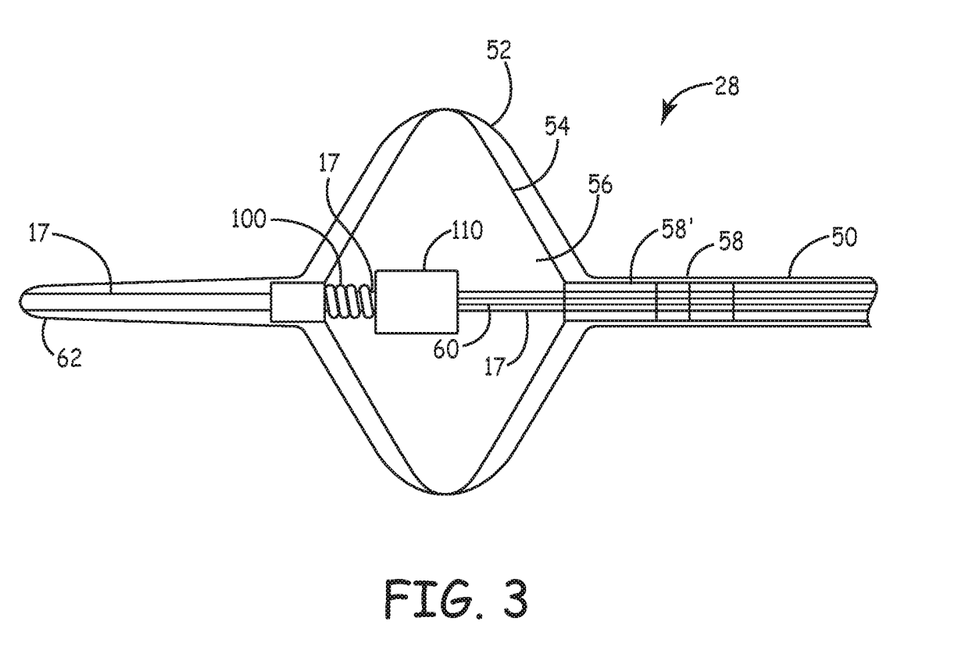
FIG. 3 depicts a longitudinal cross-sectional view of an exemplary catheter tip in accordance with an embodiment of the present disclosure is illustrated.

Turning to FIG. 3, a longitudinal cross-sectional view of an exemplary catheter tip in accordance with an embodiment of the present disclosure is illustrated. Tip 28 of the exemplary catheter 22 comprises an outer tube 50 which may be coupled to an outer balloon 52. An inner balloon 54 may be disposed within the outer balloon 52. The void within inner balloon 54 defines an expandable chamber 56. In use, both the outer balloon 52 and inner balloon 54 may be expanded concurrently to contact a blood vessel or other tissue during an ablation procedure. Although the exemplary embodiment depicts a gap between portions of the outer balloon 52 and inner balloon 54, it should be noted that the entire perimeter of both outer balloon 52 and inner balloon 54 may be in contact. The outer balloon 52 contains leaks in the inner balloon 54 should they occur. Low pressure or vacuum return lumens 58 and 58' may be in fluid communication with the interior of the outer and inner balloons, respectively.

Outer tube 50 defines a lumen that may circumferentially enclose an injection tube 60 so that the tubes may be substantially coaxially disposed with respect to each other, such that a longitudinal centerline (not shown) of outer tuber 50 approximately coincides with the longitudinal centerline (not shown) of injection tube 60. Injection tube 60 may substantially span the length of outer tube 50 and may terminate at a point slightly more distal to the absolute distal end of outer tube 50 such as within the second balloon 52. Injection tube 60 will generally be in fluid communication with the coolant injection line 36 (FIG. 2) while the return lumens 58 and 58' will typically be in fluid communication with coolant return line 38 (FIG. 2). However, other implementations in accordance with the principles set forth herein are contemplated. For example, while the injection tube 60 in fluid communication with injection line 36 have been illustrated as being separate components, other exemplary embodiments may combine both components into a unitary component.

Injection tube 60 may be disposed over a guidewire structure such as a tube, a shim or the guide wire 17 that passes through or is contained within the lumen defined by outer tube 50. The guide wire 17 is suitable for placement into the vasculature of a patient and catheter may slide over the guide wire, for guiding the distal tip 28 of the catheter 22 to a desired location using techniques known in the art. In some embodiments, the distal tip 28 can include a soft tip element 62 to minimize or prevent tissue trauma.

Figure 4:
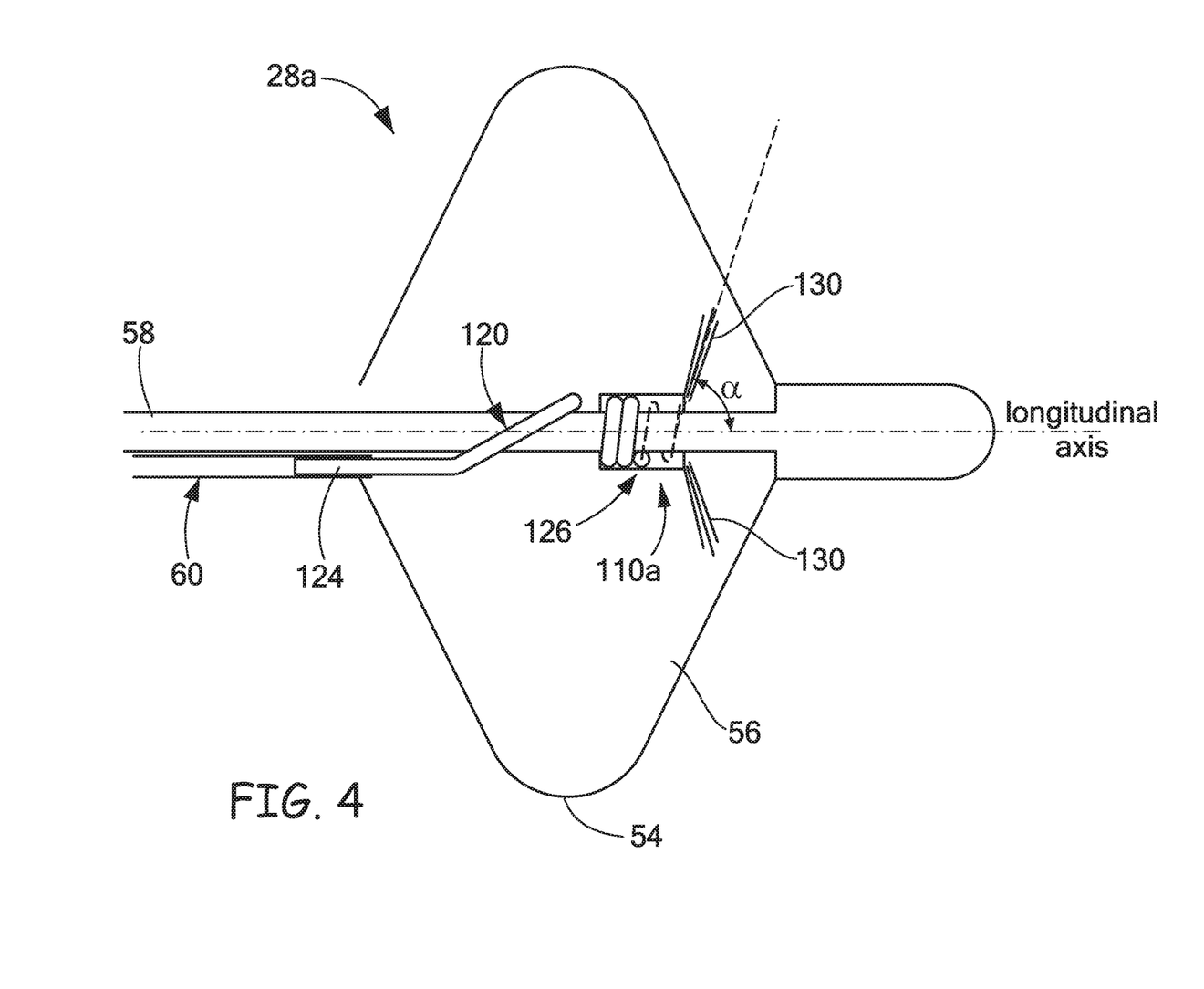
FIG. 4 illustrates an exemplary embodiment of a catheter constructed in accordance with principles of this disclosure.
Figure 5:
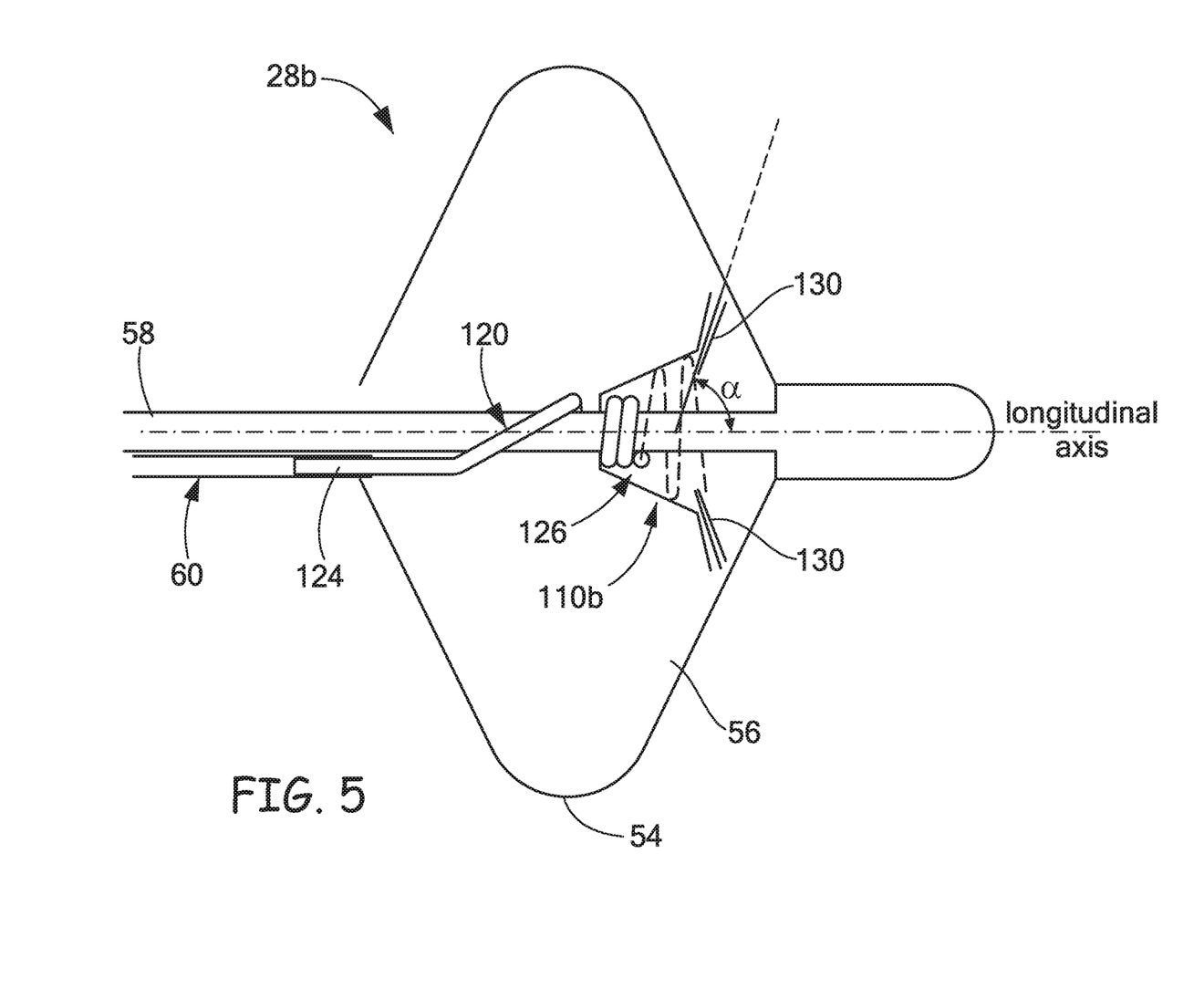
FIG. 5 illustrates an embodiment of a catheter tip constructed in accordance with the principles of this disclosure.
Figure 6:
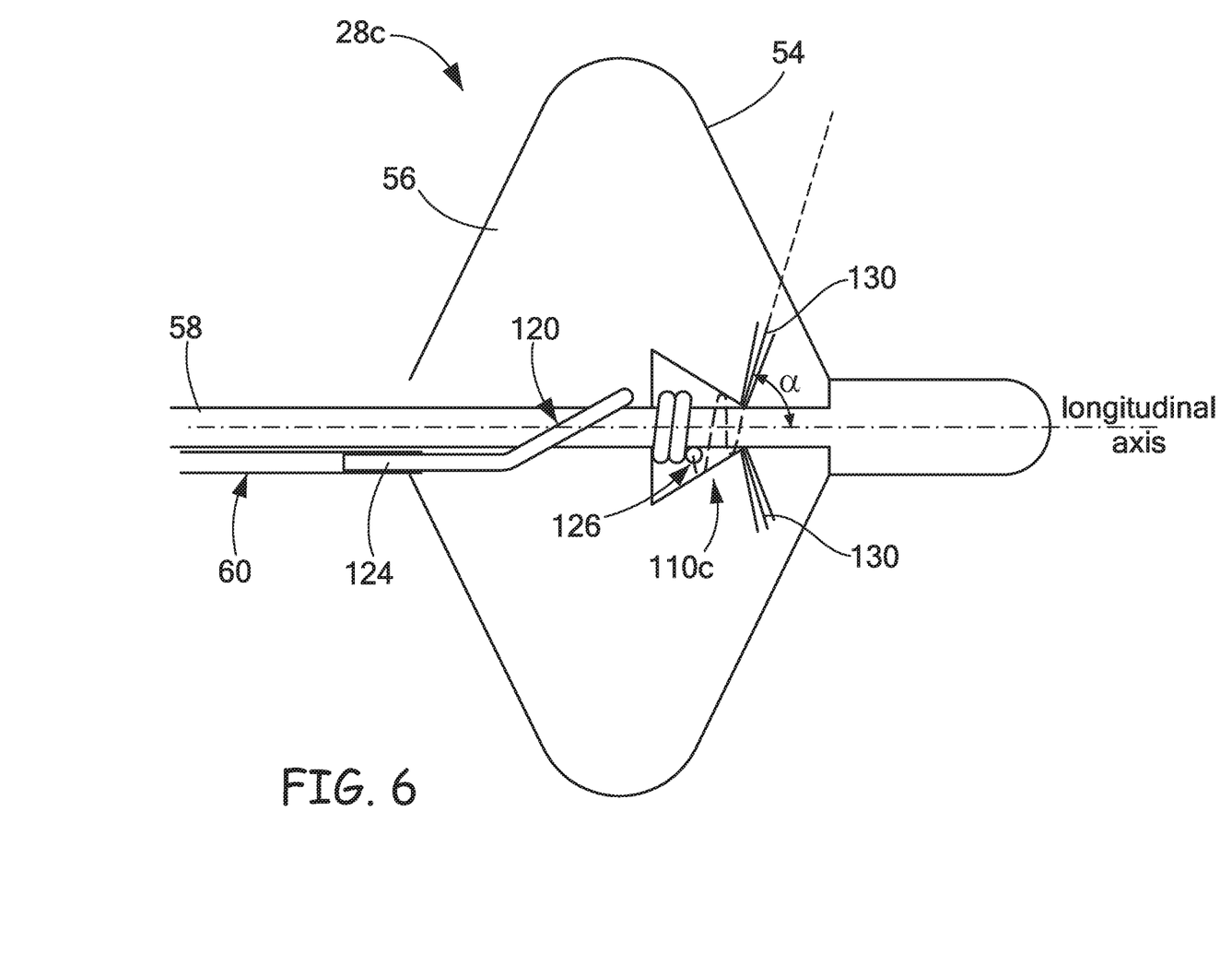
FIGS. 6-8 illustrate alternative embodiments of a catheter in accordance with the present disclosure.

A fluid dispersion unit 110 (described in more detail in conjunction with the representative embodiments of FIGS. 4-6) may be coupled to the distal portion of injection tube 20. In general, fluid dispersion unit 110 defines a chamber in which a fluid is introduced at a selected flow rate and from which the fluid is ejected in a predefined distribution pattern. Among other things, the pattern takes into account the spray angle and distribution of the fluid across a cross section of the spray. The distribution pattern will be dependent principally on the shape of the fluid dispersion unit 110. The fluid dispersion unit 110 generally directs and/or the dispersion of fluid flowing from the injection tube 60 into the expandable chamber 56 and onto an interior surface of the inner balloon 54. As such, the fluid dispersion unit 110 provides an exit point for the cryogen flowing through the injection tube 60 into the expandable chamber 56.

A compression spring 100 is further illustrated being coupled to the fluid dispersion unit 110. Any suitable material that will exhibit the desired elastic properties including, for example, stainless steel may be employed in the construction of the spring. The compression spring 100 may have a preset length that is determined by such factors as the desired location within the expandable chamber wherein the fluid contact is desired. However, in other implementations, the compression spring 100 may be moveable in an axial direction, such as through actuation with the guide wire or some other physical implement, an electrically activated actuator, fluid pressure variation, or through any other suitable means. The compression spring 100 may be selectively moveable to vary the location of the fluid dispersion unit 110. Some factors that may be taken into consideration when selecting the location of the fluid dispersion unit 110 will include the spray diameter and the desired contact location within inner balloon 54.

FIG. 4 illustrates an exemplary embodiment of a catheter constructed in accordance with principles of this disclosure. The depiction shows an implementation where the injection tube 60 is coupled to a refrigerant coil 120. A proximal portion 124 of the refrigerant coil 120 is coupled to the distal end of the injection tube 60 to provide a continuous lumen for flow of a fluid therein. The refrigerant coil 120 terminates with a coil outlet or flow nozzle 126 at a terminal distal portion 122. The distal portion 122 of the refrigerant coil 120 may be shaped to induce in a fluid passing therethrough a predetermined motion. For example, the distal portion 122 may be coiled or wound in a helical, spiral, curvilinear, or coiling configurations to induce a correspondingly shaped motion for example. In some embodiment, the coil pitch may also be varied to achieve the desired fluid motion.

In other embodiments, inducing a selected shaped motion is achieved by the interaction of fluid flowing from portion 122 with the fluid dispersion unit 110. This may be through, for example, disposing the tip of portion 122 terminating at the flow nozzle 126 within fluid dispersion unit 110 such that the fluid will flow tangentially to the longitudinal axis of fluid dispersion unit 110. For example, at least the distal tip of portion 122 may be aligned in an orthogonal axis in relation to the longitudinal axis of the fluid dispersion unit 110 to induce a swirling motion in the fluid exiting from the fluid nozzle 126 within the fluid dispersion unit 110.

Continuing with the depiction of FIG. 4, fluid dispersion unit 110a is formed as a tubular-shaped sleeve that encloses the distal portion 122 of refrigerant coil 120 in a catheter tip 28a. The exemplary sleeve of unit 110a may be formed from a material such as stainless steel or polyimide. A proximal end 112 of fluid dispersion unit 110a may be sealed to prevent the expulsion of a fluid medium through the proximal end 112, in one example. In some examples, a portion (or the entire) interior surface of the sleeve may be coated with a hydrophobic material. The hydrophobic material will facilitate the repulsion of the fluid medium flowing through the fluid dispersion unit 110a and thereby reduce the capillary effect associated with fluid agglomeration such as at the distal tip of the fluid dispersion unit 110a.

With that in mind, a high pressure, low temperature fluid is typically supplied to the catheter 22, and initially enters the catheter 22 as it flows through the injection tube 60 towards the expandable chamber 56. Conventional injection tubes generally have one or more orifices from which the fluid will flow. However, the location at which the fluid contacts inner balloon 54 as it is ejected from the orifice will vary depending on the orientation of the injection tube 60, the size to which the balloons have been expanded, and even the orientation, size and location of the orifice.

In the present embodiment, the fluid will upon flowing through the injection tube 60, exit the injection tube 60 through the outlet 126. The fluid being expelled from outlet 126 will come in contact with the interior surface of fluid dispersion unit 110a at an angle that is dependent on the orientation of the distal tip of portion 122. For instance, outlet 126 may be configured to direct the flow of fluid into the fluid dispersion unit 110a in an angle that is tangential to the longitudinal axis of the fluid dispersion unit 110a (depicted as angle α in FIGS. 4-8). As such, the fluid exiting outlet 126 will be caused to spin in a predetermined motion with the motion being dependent on the shape of the fluid dispersion unit 110a. The spin velocity of the fluid will increase as the fluid approaches the distal tip of the fluid dispersion unit 110a. However, all of the pressure of the fluid supplied by the injection tube 60 is not all converted into velocity energy. Some of the energy is maintained as pressure energy which will tend to push the fluid distally toward the distal tip of fluid dispersion unit 110a. This pressure urges the fluid to attain a predetermined spray pattern because of the centrifugal force. As such, the fluid is ejected at the distal end of unit 110a into the expandable chamber 56 in the predetermined spray pattern 130. In other words, as the fluid spins toward the distal end of the fluid dispersion unit 110a, the centrifugal force exerted on the fluid as it rotates through fluid dispersion unit 110a will result in the fluid being dispersed from the fluid dispersion unit 110a in a motion that will cover a 360 degree angle. After flowing into the expandable chamber 56, the fluid is induced, through a negative pressure gradient, to flow back towards the proximate portion of the catheter 22 through the return lumen 58'.

The length and diameter of the fluid dispersion unit 110a may be selected during construction to control the angle of dispersion of fluid from the distal end. In addition, the location of the outlet 126 within fluid dispersion unit 110a may also be varied to control the angle of dispersion and conversely the fluid dispersion unit 110a may be moveable with the expandable chamber 56 to vary the angle of dispersion. It should be noted that the angle of dispersion of fluid from fluid dispersion unit 110a directs the fluid in a desired direction and hence controls the location of contact of the fluid with inner balloon 54. Therefore, the location of the fluid dispersion unit 110a within expandable chamber 56 may also be varied as previously described with the compression spring 100 to channel the fluid to a desired location. As illustrated schematically by the arrows, the spray pattern 130 in the expandable chamber will generally cause the fluid to come in contact with a preselected portion of the inner balloon 54. As such, in ablation procedures, adjustment of the angle of dispersion of fluid from fluid dispersion unit 110a adjusts the angle of fluid dispersion, and hence the location of contact, to target the ablation zone.

Additionally, because the angle of the fluid that is ejected from the fluid dispersion unit 110a depends mainly on the velocity vector of the fluid (axial speed as opposed to radial speed), the angle of the distal portion 122 leading to outlet 126 can be varied to provide a different angle of distribution of fluid being dispersed from the distal end of fluid dispersion unit 110a.

The fluid dispersion unit 110 may be embodied in other shapes configured to direct the flow of coolant in a predetermined direction and/or pattern.

FIG. 5 illustrates an alternative embodiment of the catheter 22. Specifically, a catheter tip 28b is depicted with a fluid dispersion unit 110b having a conical shape. The desired shape will be selected such that a desired flow pattern is induced in the fluid exiting the outlet 126 and contacting the inner surface of the fluid dispersion unit. The fluid, thereby predisposed to have a given pattern, will be expelled from the fluid dispersion unit 110b to preselected locations on the inner balloon 54.

FIG. 6 illustrates another exemplary embodiment of the catheter 22. In the embodiment, a catheter tip 28c includes a fluid dispersion unit 110c having an inverted conical shape wherein the diameter of the proximal end is larger than the diameter of the distal end.

Figure 7:
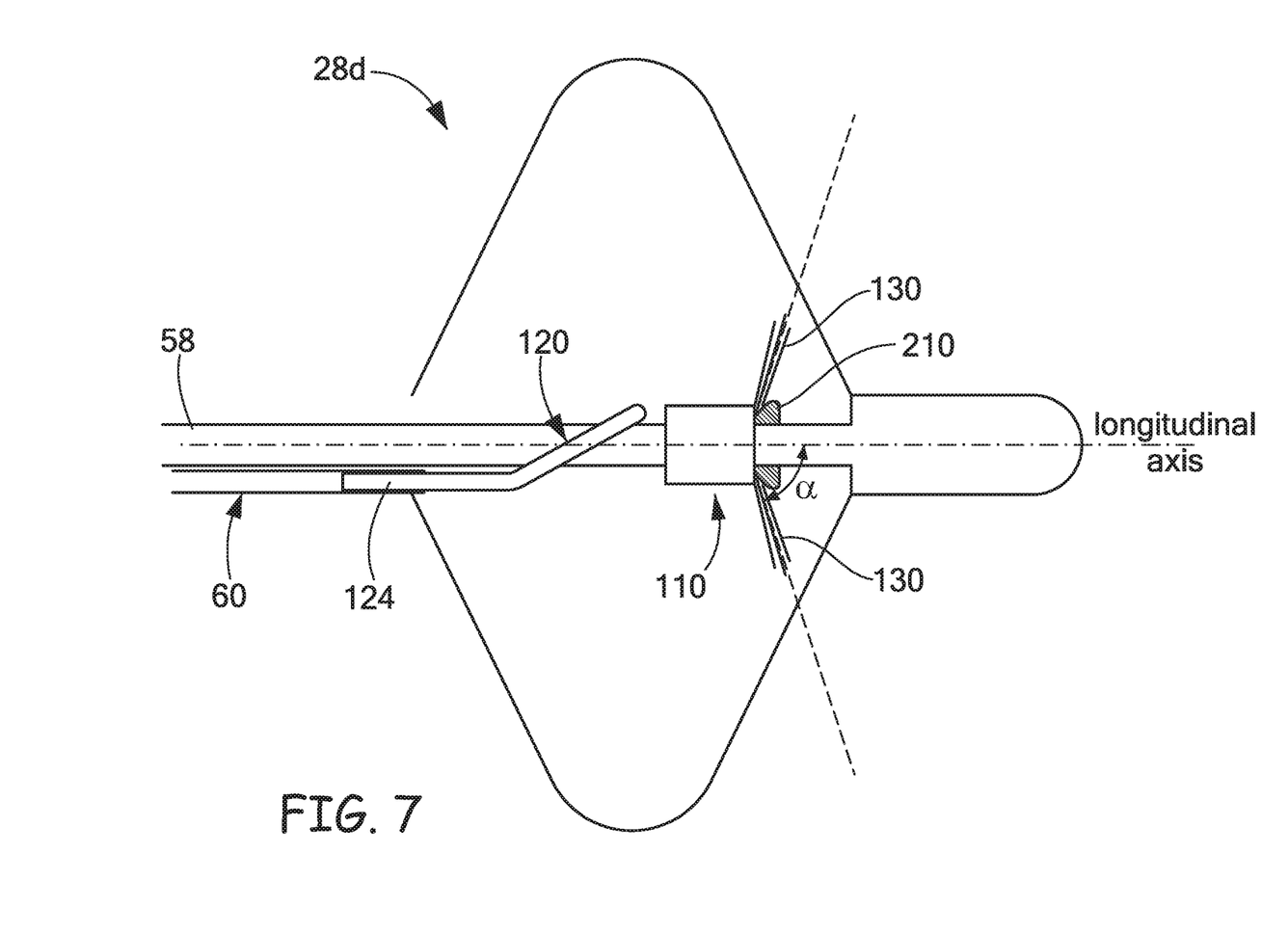

FIG. 7 illustrates an alternative embodiment of the catheter 22 in accordance with the present disclosure. In accordance with other aspects of the disclosure, it is contemplated that a fluid dispersion unit such as the aforementioned fluid dispersion unit 110a, fluid dispersion unit 110b, or fluid dispersion unit 110c (collectively "fluid dispersion unit 110") may be alternatively employed in this embodiment. A catheter tip 28d includes fluid dispersion unit 110 that cooperates with a deflector member 210 both of which are disposed within the expandable chamber 56. The deflector member 210 is positioned at a suitable distance distal of the dispersion unit 110 to condition flow of the fluid leaving dispersion unit 110. As depicted in the illustrative embodiment of FIG. 7, deflector member 210 is embodied as a guide flange having an inclined plane with the inclined surface channeling the flow of fluid expelled from the dispersion unit 110 along a defined path. The length and incline of deflector member 210 may be configured to extend along an axial direction so as to channel the fluid to specific locations along the inner circumference of the inner balloon 54 while preventing dripping onto undesired portions of the inner balloon 54. As such, the deflector member 210 may enhance the control of the flow directionality of a fluid ejected from the fluid dispersion unit 110.

Figure 8:
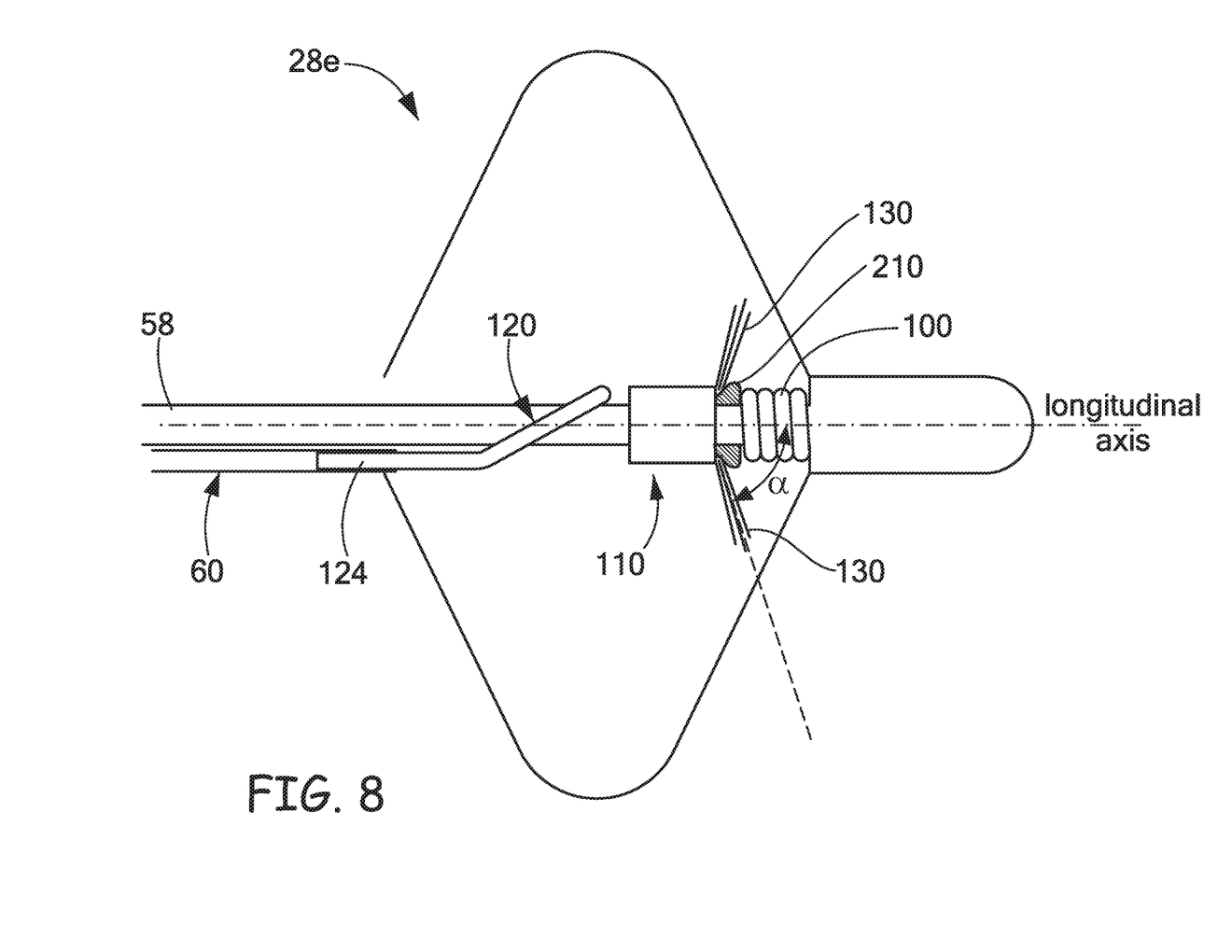

FIG. 8 depicts yet another alternative embodiment of the catheter in accordance with the present disclosure. In the illustration, a catheter tip 28e includes fluid dispersion unit 110 that cooperates with deflector member 210 as described with reference to FIG. 7. The deflector member 210 is further coupled to compression spring 100. The compression spring is moveable along an axial direction to influence the location of the deflector member 210 within the expandable chamber 56. For example, the pressure of the cryogen fluid expelled from the refrigerant coil 120 may be selectively-adjusted so as to cause extension/contraction of the spring 100 to a desired length. The contraction/expansion of the spring 100 also causes a reciprocal movement of the deflector member 210 and thereby regulates the position of the deflector member 210 within the expandable chamber 56. Other suitable mechanisms for compression/expansion of the compression spring 100 such as those described in conjunction with FIG. 3 may alternatively be employed.

It should be noted that a wide variety of spray patterns and spray angles may be achieved by any one of the various exemplary fluid dispersion units disclosed herein. Thus, for any given implementation, such factors as the distance between the distal tip of fluid dispersion unit 110 to the desired fluid contact location on inner balloon 54, the circumference of the fluid dispersion unit 110, the length of the fluid dispersion unit 110, the flow rate of fluid flowing from the injection tube 60, or the pressure of fluid flowing from the injection tube 60 can all be varied. For example, a hollow cone spray pattern in which the fluid concentration is at the outer edge of the cone with little or no fluid in the center may be generated by the tubular fluid dispersion unit 110 in which a cylindrical chamber causes the fluid to spin and achieve the hollow cone pattern. The spray angle and hence the diameter of the contact points between the expelled fluid and the inner balloon 54 can be varied by adjusting the various aforementioned factors such as coil angle and coil pitch.

The preceding specific embodiments are illustrative of the practice of the aspects of the disclosure. Various modifications can be made without departing from the scope of the claims. For example, in embodiments where a refrigerant coil 120 is not utilized, the distal portion of injection tube 60 may suitably be shaped as described with respect to the distal portion 122 of refrigerant coil 120 to induce similar motions in a fluid exiting through a nozzle of the tube 60. The similarly shaped distal portion of the injection tube 60 may then be enclosed within the fluid dispersion unit 110 to facilitate fluid expulsion as described above. Various examples for controlling the dispersion of fluid from a catheter have been described. These and other examples are within the scope of the disclosure defined by the following claims.

What is claimed is:

1. A cryoablation device comprising:
an expandable element defining a chamber;
an injection tube in fluid communication with the chamber, the injection tube having a proximal portion couplable to a source of cryoablation fluid and a distal portion within the chamber, the distal portion of the injection tube including a terminal distal portion with an outlet; and
a fluid dispersion unit surrounding at least a portion of the distal portion of the injection tube and having a longitudinal axis, the outlet of the injection tube being located within the fluid dispersion unit and being configured to direct a flow of fluid into the fluid dispersion unit in a direction that is tangential to the longitudinal axis of the fluid dispersion unit, the fluid dispersion unit having a distal opening and a conical shape.

2. The cryoablation device of claim 1, wherein the cryoablation device further comprises an elongated body having a distal portion and a proximal portion, the expandable element being coupled to the distal portion of the elongated body.

3. The cryoablation device of claim 2, further comprising a guidewire tube located within the elongated body and extending into the chamber, the distal portion of the injection tube being coiled around at least a portion of the guidewire tube.

4. The cryoablation device of claim 1, wherein the expandable element is a balloon having an inner surface.

5. The cryoablation device of claim 4, wherein the fluid dispersion unit is configured to direct a flow path of fluid expelled by the outlet of the injection tube in a pattern within the fluid dispersion unit and onto the inner surface of the balloon.

6. The cryoablation device of claim 1, wherein the expandable element comprises an inner balloon disposed within an outer balloon, the inner balloon having an inner surface and defining the chamber.

7. The cryoablation device of claim 1, further comprising a compression spring located distal to the fluid dispersion unit and within the chamber.

8. The cryoablation device of claim 7, wherein the compression spring is selectively movable along the longitudinal axis of the fluid dispersion unit.

9. The cryoablation device of claim 7, further comprising a deflection element distal to the fluid dispersion unit and proximal to the compression spring.

10. The cryoablation device of claim 9, wherein the deflection element is a guide flange having an inclined plane that channels a flow of fluid from the fluid dispersion unit along a defined path.

11. The cryoablation device of claim 10, wherein the deflection element extends along an axial direction such that the deflection element channels the flow of fluid to predetermined locations within the chamber and prevents the flow of fluid to undesired locations within the chamber.

12. The cryoablation device of claim 7, wherein the fluid dispersion unit is coupled to the compression spring.

13. The cryoablation device of claim 7, wherein the fluid dispersion unit is configured to direct a flow path of the flow of fluid expelled by the outlet of the injection tube in one of a circular pattern and an arcuate pattern.

14. The cryoablation device of claim 1, wherein the fluid dispersion unit comprises a flow distribution sleeve having a distal end that at least partially extends past a distal tip of the outlet of the injection tube.

15. The cryoablation device of claim 14, wherein an interior surface of the flow distribution sleeve is coated with a hydrophobic material.

16. The cryoablation device of claim 14, wherein the flow distribution sleeve is shaped to induce in the cryoablation fluid exiting through the outlet of the injection tube a 360 degree pattern within the chamber.

17. A cryoablation device comprising:
an expandable element defining a chamber;
an injection tube in fluid communication with the chamber, the injection tube having a proximal portion couplable to a source of cryoablation fluid and a distal portion within the chamber, the distal portion of the injection tube including a terminal distal portion with an outlet; and
a fluid dispersion unit surrounding at least a portion of the distal portion of the injection tube and having a longitudinal axis, the outlet of the injection tube being located within the fluid dispersion unit and being configured to direct a flow of fluid into the fluid dispersion unit in a direction that is tangential to the longitudinal axis of the fluid dispersion unit, the fluid dispersion unit having a distal opening and an inverted conical shape.

18. The cryoablation device of claim 17, further comprising an elongated body and a guidewire tube located within the elongated body and extending into the chamber, the distal portion of the injection tube being coiled around at least a portion of the guidewire tube.

19. The cryoablation device of claim 17, further comprising a deflection element distal to the fluid dispersion unit.

20. The cryoablation device of claim 17, wherein an inner surface of the fluid dispersion unit is coated with a hydrophobic material.

* * * * *